United States Patent [19]

Wong

[11] Patent Number: 5,060,508
[45] Date of Patent: Oct. 29, 1991

[54] GAS SAMPLE CHAMBER

[75] Inventor: Jacob Y. Wong, Santa Barbara, Calif.

[73] Assignee: Gaztech Corporation, Goleta, Calif.

[21] Appl. No.: 503,216

[22] Filed: Apr. 2, 1990

[51] Int. Cl.⁵ .............................................. G01N 30/02
[52] U.S. Cl. .................................. 73/31.02; 356/437
[58] Field of Search ........... 73/863.33, 863.81, 863.83, 73/31.01, 31.02, 31.05, 431; 356/436–441; 250/432 R, 437; 340/630; 29/463

[56] References Cited

U.S. PATENT DOCUMENTS

| | | | |
|---|---|---|---|
| 3,893,601 | 7/1975 | Winslow | 29/463 |
| 3,922,656 | 11/1975 | Horvath et al. | 356/439 |
| 3,950,980 | 4/1976 | Braun et al. | 73/31.05 |
| 4,235,097 | 11/1980 | Kring et al. | 73/31.02 |
| 4,554,721 | 11/1985 | Carty et al. | 29/463 |
| 4,700,079 | 10/1987 | Ito | 356/438 |
| 4,709,150 | 11/1987 | Burough et al. | 356/437 |
| 4,905,497 | 3/1990 | Shindo et al. | 73/1 G |
| 4,946,092 | 8/1990 | van Poorten | 29/463 |

FOREIGN PATENT DOCUMENTS

| | | | |
|---|---|---|---|
| 3031285 | 3/1981 | Fed. Rep. of Germany | 340/630 |
| 0105946 | 6/1985 | Japan | 356/437 |
| 0280638 | 12/1987 | Japan | 356/440 |

Primary Examiner—Robert Raevis
Attorney, Agent, or Firm—Daniel C. McKown

[57] ABSTRACT

A sample chamber for use in measuring the absorption of radiation as it passes through a gas within the chamber includes a block having an extended serpentine passage through it. The walls of the extended passage are coated with a highly reflective material so that the extended passage acts as a light pipe for transmitting the radiation. A number of smaller passages permit gases in the space surrounding the sample chamber to diffuse into the extended passage through which the radiation is conducted. The sampling chamber is made by joining two halves, each of which has a planar face in which an elongated groove is produced. The halves are molded of plastic and in quantity the chamber is quite inexpensive.

13 Claims, 1 Drawing Sheet

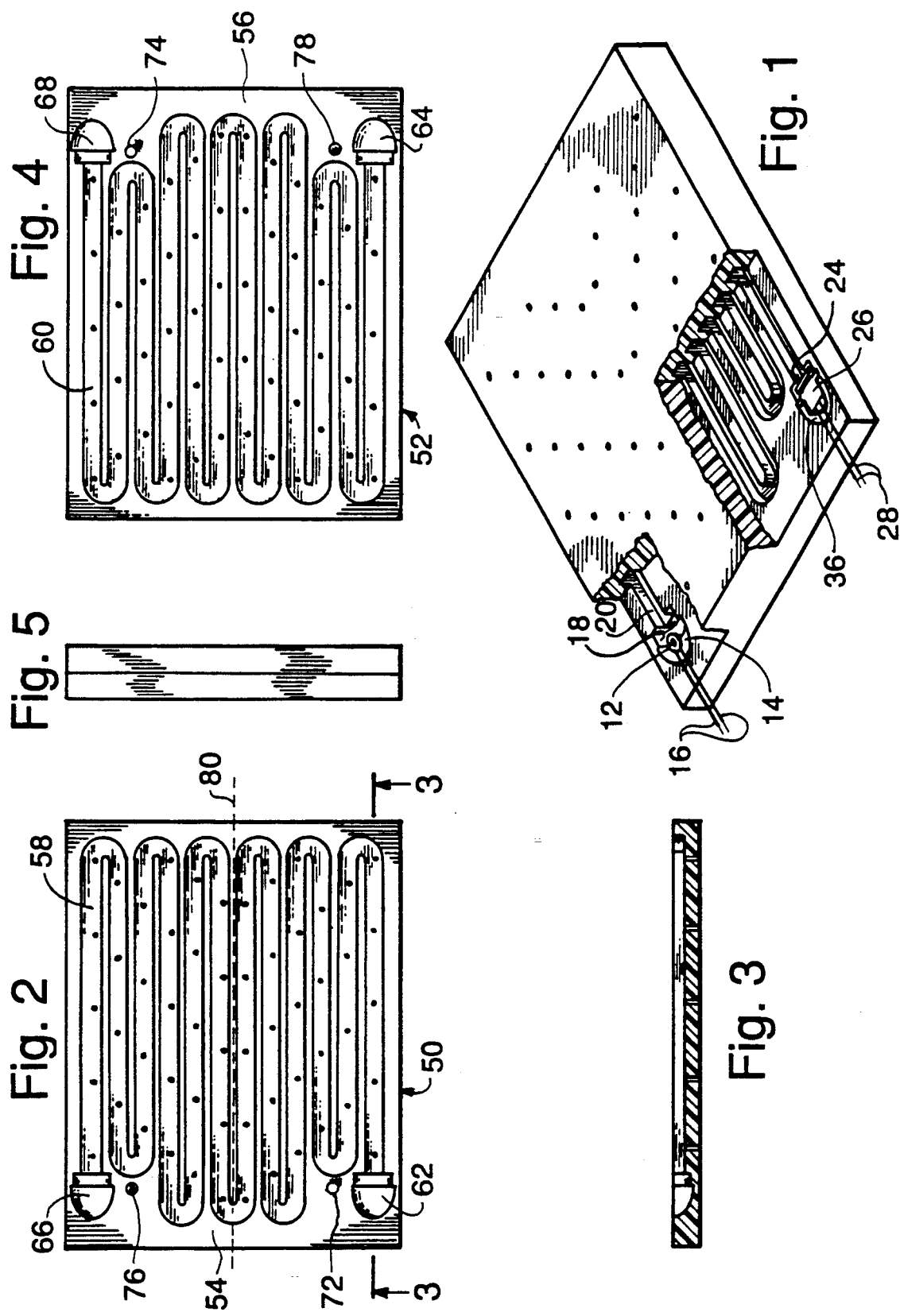

GAS SAMPLE CHAMBER

BACKGROUND OF THE INVENTION

1. Field of the Invention

The present invention is in the field of gas analysis and more particularly relates to a compact sample cell for use in measuring very small concentrations of a gas based on the absorption of light or other radiation as it passes through the gas within the sample cell.

2. The Prior Art

Certain gases have absorption bands that absorb so weakly that absorption can only be detected after the radiation has traveled a relatively long distance, perhaps tens of meters, through the gas. In other situations the gases of interest might have adequate absorption strengths but they must be detected in very low concentrations, typically in parts per million (ppm) or less, so that long path lengths are required in this situation also.

Practical gas analyzers for commerical use seldom incorporate very long path-length sample cells for such purposes primarily because of size limitations. Where the use of long path-length sample cells cannot be avoided, it is common to use mirrors to fold an optical beam so that the latter can traverse the sample cell a number of times.

A multi-path absorption cell was described by J. U. White, Journal of Optical Society of America, Volume 32, page 285 (1942). The essential parts of the White cell consist of three spherical concave mirrors all having the same radius of curvature and positioned to form an optical cavity. Utilizing the principle outlined in White's article, at least two companies have marketed a ten-meter multi-path cell, and one of the companies has also marketed a forty-meter multi-path cell.

In U.S. Pat. No. 4,756,622 Wong disclosed another approach for providing long path-lengths for measuring the absorption by a gas. In Wong's invention, light is made to travel through a limited volume of gas a large number of times. The light is placed on a closed optical path on which it circulates through the gas sample. After a desired number of passes through the gas sample, the light is removed from the closed optical path. Introduction of the light to the closed optical path and removal therefrom is accomplished through the use of a polarizing beamsplitter and a Pockels cell located on the closed path. Light is put onto the closed path by the polarizing beamsplitter which imparts a specific polarization. During the first circuit the Pockels cell alters the polarization by 90 degrees thereby preventing the light from escaping back out through the polarizing beamsplitter. After the desired number of circuits, the Pockels cell again alters the polarization by 90 degrees thereby permitting the light to be redirected out of the closed path by the polarizing beamsplitter.

While the White cell and Wong's invention work well in certain specific applications, they both suffer from the disadvantages of being complex and expensive. They are therefore not practical for use in low-cost mass-oriented applications such as in toxic gas monitors (e.g., carbon monoxide, ozone, nitric oxide, etc.) where low ppm detection is often required. Furthermore, in both of the above devices, the gas whose concentration is to be measured has to be introduced into the sample cell via a cumbersome vacuum pump.

The success of Non-Dispersive Infrared (NDIR) techniques in gas analysis has led the present inventor to consider the application of this technology to the design and construction of new fire detectors. The technique involves detecting the rapid build-up of low concentrations of carbon dioxide and carbon monoxide gases in the ambient air caused by the fires.

The concentrations of these gases that need to be detected lie typically in the tens to hundreds of ppm. Because concentrations are so low, long path-length sample chambers are required.

The complex and expensive multi-path sample cells mentioned previously are clearly not suitable for this type of application. A simple and low-cost long path-length sample cell, which is currently not available commerically to the best of our knowledge, is needed instead.

SUMMARY OF THE INVENTION

A major purpose of the present invention is to provide a simple, low-cost and long path-length sample cell suitable for the measurement of very low concentrations of gases (such as carbon dioxide) having medium to strong absorption bands in the infrared.

Another purpose of the present invention is to eliminate under certain favorable measuring conditions the need for using a vacuum pump or similar device to introduce the gas to be measured into the sample chamber.

Another purpose of the present invention is to simplify the construction of the sample cell by the use of symmetry, so that the system source and detector can be included integrally into the sample cell structure, which comprises only two identical parts joined together symmetrically to form a single unit.

In accordance with the present invention, the infrared radiation is introduced into a sample chamber that includes a long and serpentine hollow tube having a uniform cross section and highly reflecting walls.

Taking advantage of symmetry, the serpentine hollow tube structure is formed by bonding together two identical plates, the mating faces each furrowed by an extended groove that constitutes one-half of the hollow serpentine tube. Furthermore, the source and detector cavities are interchangeable so that when the two identical plates are bonded together both the source and the detector are captured integrally into the sample cell structure.

A number of small passages extend perpendicular to the mating surfaces and permit the ambient air to enter the hollow serpentine sample chamber by diffusion.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view partly cut away and showing a gas sample chamber in accordance with the present invention;

FIG. 2 is a plan view showing a first half of the gas sample chamber in a preferred embodiment of the present invention;

FIG. 3 is a side elevational cross sectional view in the direction 3—3 indicated in FIG. 2;

FIG. 4 is a plan view showing a second half of the gas sample chamber in a preferred embodiment; and, FIG. 5 is an end view of the gas sample chamber in a preferred embodiment.

DETAILED DESCRIPTION OF THE PREFERRED EMBODIMENT

The perspective view of FIG. 1 shows the external appearance of the gas sample chamber of the present invention as well as certain internal features of it. In essence, the gas sample chamber, when assembled, is a block 22 through which a passage 20 extends along an indirect path. At a first end of the passage a chamber 14 is provided, into which an electrically powered source of radiation 12 is mounted. The electricity for operating the source is supplied through the conductors 16.

In the preferred embodiment, the chamber 14 for the source is bounded by an ellipsoidal mirror 18. The source 12 is located at one focus of the ellipsoid, and radiation from the source is concentrated by the ellipsoidal mirror 18 to the opposite focus, which lies within the extended passage 20. This arrangement assures an efficient coupling of the radiation produced by the source 12 to the extended passage 20.

The walls of the extended passage 20 have a mirror-like finish and in some embodiments are coated with a highly reflecting material. The radiation that has been directed into the extended passage 20 will therefore progress by successive reflections through the passage, and a fraction of the radiation will reach the other end of the passage, which is provided with a detector chamber 36. The detector package 26 includes a filter 24 which selectively passes radiation of certain wavelengths, and further includes a detector element which converts the radiation that has passed through the filter 24 into an electrical signal which is brought out of the gas sample chamber on the conductors 28.

A number of passages, of which the passage 30 is typical, permit communication between the extended passage 20 and the air in the space surrounding the gas sample chamber. The gas whose concentration is to be measured enters the extended passage 20 by diffusion through the passages 30.

Although FIG. 1 shows the gas sample chamber with the source of radiation 12, the detector 26 and the filter 24 installed in it, it should be understood that the gas sample chamber itself does not include those components, which are shown in FIG. 1 to demonstrate how the gas sample chamber is used.

In theory the gas sample chamber of FIG. 1 could be produced from a single block of material by a lost wax process or similar casting method. However, the present inventor has found an efficient way of manufacturing the sample chambers, and that technique is shown in FIGS. 2-5 which illustrate the preferred embodiment of the present invention.

In accordance with the preferred embodiment, the gas sample chamber is formed by bringing together two halves 50 and 52 shown respectively in FIGS. 2 and 4, and joining the halves by bonding them together.

Referring to FIG. 2, the first half 50 includes a planar face 54 into which an elongated groove 58 extends. In the preferred embodiment, the extended passage 20 has a square cross section. A portion 62 of the detector chamber and a portion 66 of the source chamber are formed at the ends of the elongated groove.

In theory, the elongated groove and the detector chamber and source chamber could be machined into the first half 50, but in the preferred embodiment they are molded into the first half, which is composed of a plastic.

Similarly, as shown in FIG. 4, a second half 52 is produced having a planar face 56, an elongated groove 60 and portions 64 and 68 of the detector and source chambers, respectively.

FIG. 3 is a cross sectional view in the direction 3—3 indicated in FIG. 2.

FIG. 5 is an end view showing the halves 50 and 52 after they have been brought together.

It is important that the halves 50 and 52 register rather accurately when brought together. In one variation of the preferred embodiment, the edges of the blocks are used to register the halves. In another variation, pins 72 and 74 are provided, which slide into the holes 76 and 78 when the halves are brought together.

The elongated grooves 58 and 60 in the first half 50 and the second half 52 are coated with a thin metallic layer by electroless plating or by vacuum deposition using nickel, aluminum, or chromium. When this is done, the wall reflectivity is on the order of 0.95 in the near infrared.

In the preferred embodiment of FIGS. 2-5, the path length through the extended passage 20 is approximately ten times the length of the block 22. This ratio is a trade-off between the diminishing intensity that results as the path is made longer against the increased absorption that is available with the longer path length. In theory, the passage 20 could be made longer or shorter in accordance with the particular gas to be detected and in accordance with the intensity of the source 12 and the sensitivity of the detector 26.

When manufactured by the molding technique used in the preferred embodiment, the gas sample cells are quite inexpensive.

The juxtaposition of FIGS. 2, 4 and 5 is intended to illustrate that the manufacturing technique of the preferred embodiment requires only that the grooved pattern formed in the first half 50 be a mirror image of the grooved pattern form in the second 52. In general, the halves will not be identical, but instead will be related as the left hand is related to the right hand.

The present inventor further improved on the design by noting that if the groove pattern on each half were bilaterally symmetric with respect to an imaginary line 80 on the planar face of each half, then the two halves will be identical. This observation permits the use of a single mold instead of two molds (left and right). It also simplifies logistics and handling because the halves do not have to be identified as being left or right.

Thus, there has been described a gas sample chamber that provides a path length that is many times the length of the chamber, and that is inexpensive to manufacture and that is easy to use because it readily accommodates radiant sources and detectors that are widely used.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A sample chamber comprising:

a first block having a planar face and having an elongated groove of uniform depth in said planar face, the length of said elongated groove exceeding the largest dimension of said first block;

a first passage extending transversely from said elongated groove clear through said first block;

a second block having a planar face and having an elongated groove of uniform depth in said planar face, said elongated groove being the mirror image of the elongated groove in said first block, so that when said first block and said second block are brought together to form a combined block with the planar face of said first block lying against the planar face of said second block, the elongated grooves can be brought into registration to form an elongated passage in the combined block; and, a second passage extending transversely from said elongated groove of said second block clear through said second block, said second passage in combination with said first passage facilitating diffusion of a gas into and out of said elongated passage in the combined block.

2. The sample chamber of claim 1 further comprising a reflective coating on the elongated groove of said first block and on the elongated groove of said second block.

3. The sample chamber of claim 1 wherein the elongated groove of said first block follows a serpentine path in said planar face of said first block.

4. The sample chamber of claim 1 wherein the elongated groove of said first block has a rectangular cross section.

5. The sample chamber of claim 1 wherein first passage through said first block is approximately perpendicular to said planar face of said first block.

6. The sample chamber of claim 1 wherein said second passage through said second block is approximately perpendicular to said planar face of said second block.

7. The sample chamber of claim 1 wherein said first block further includes portions defining a detector chamber at one end of said elongated groove.

8. The sample chamber of claim 7 wherein said first block further includes portions of said detector chamber defining a mirror.

9. The sample chamber of claim 1 wherein said first block further includes portions defining a source chamber at one end of said elongated groove.

10. The sample chamber of claim 9 wherein said first block further includes portions of said source chamber defining a mirror.

11. The sample chamber of claim 1 wherein said first block further includes portions defining means for registering the elongated groove of said first block with the elongated groove of said second block.

12. A sample chamber comprising:

a block including portions defining an extended passage entirely enclosed within said block, the length of said extended passage exceeding the largest dimension of said block;

a reflective coating on said portions defining an extended passage; and, at least two passages extending transversely from said extended passage in opposite directions through said block to the exposed surface of said block to facilitate diffusion of a gas into and out of said extended passage.

13. A sample chamber comprising:

a block including portions defining an extended passage entirely enclosed within said block, the length of said extended passage exceeding the largest dimension of said block;

said block further including portions defining a source chamber within said block at one end of said extended passage, portions of said source chamber defining a mirror; and, at least two passages extending transversely from said extended passage in opposite directions through said block to the exposed surface of said block to facilitate diffusion of a gas into and out of said extended passage.

* * * * *